US005763664A

United States Patent [19]
Saunders

[11] Patent Number: 5,763,664
[45] Date of Patent: Jun. 9, 1998

[54] PROCESS FOR PREPARING CYCLOPENTENONES

[75] Inventor: Paul C. Saunders, Baton Rouge, La.

[73] Assignee: Albemarle Corporation, Richmond, Va.

[21] Appl. No.: 566,097

[22] Filed: Dec. 1, 1995

[51] Int. Cl.$^6$ .................................................. C07C 49/105
[52] U.S. Cl. .................................................. 568/379
[58] Field of Search .................................. 568/338, 343, 568/353, 379

[56] References Cited

U.S. PATENT DOCUMENTS

| | | |
|---|---|---|
| 3,907,896 | 9/1975 | Calame. |
| 4,384,144 | 5/1983 | Shono et al. ........................... 568/347 |
| 4,413,145 | 11/1983 | Piancatelli et al. ...................... 568/345 |
| 5,026,919 | 6/1991 | Dessau .................................... 568/433 |
| 5,276,199 | 1/1994 | Lee. |

OTHER PUBLICATIONS

Rosini, G., et al., "A New Route to 1,4–Diketones and its Application to (Z)–Jasmone and Dihydrojasmone Synthesis", Tetrahedron vol. 39, No. 24, pp. 4127–4132 (1983).

Acheson, R. M., et al., "Experiments Bearing on the Synthesis of Cortisone, Part I,* Some Cyclopentenone Derivatives", J. Chem. Soc., pp. 1127–1133—1133 (1952).

*Primary Examiner*—Gary Geist
*Assistant Examiner*—Karl J. Puttlitz, Jr.
*Attorney, Agent, or Firm*—Philip M. Pippenger

[57] ABSTRACT

A process for preparing a cyclopentenone by forming a two-phase mixture of a 1,4-diketone, a water immiscible organic solvent, and an aqueous base solution, and heating the mixture so as to convert the 1,4-diketone to a cyclopentenone which collects in the organic solvent phase.

15 Claims, No Drawings

PROCESS FOR PREPARING CYCLOPENTENONES

This process relates generally to the preparation of cyclic ketones and more specifically to the preparation of hydrocarbyl substituted cyclopentenones from 1,4-diketones.

Cyclopentenones are useful compounds for preparing hydrocarbyl substituted cyclopentadienes which can be reacted with transition metal salts to form metallocene catalysts for olefin polymerization. It is known to make cyclopentenones, such as 3-methylcyclopent-2-en-1-one, by heating a 1,4-diketone, such as acetonylacetone, with base, such as NaOH. The product is unstable in the presence of base. Consequently, either care must be taken to avoid excessive tar formation or the product must be removed as it is formed, for example, by distillation as described in U.S. Pat. No. 3,907,896.

An improved process is described in U.S. Pat. No. 5,276,199 in which a two-phase mixture of a 1,4-diketone, a water immiscible organic solvent and an aqueous base solution is formed and the mixture is heated so as to convert the 1,4-diketone to a cyclopentenone which collects in the organic solvent phase. This process can be carried out at lower temperatures and does not involve the contemporaneous removal of product from the reaction mixture. The improvement also provides a practical process in which the reactor-loading can be 5–10 times higher than in the process according to the 3,907,896 patent.

The two-phase reaction system has now been improved to provide higher yields of product, while reducing tar formation and providing an easier work-up. Instead of precharging all of the ketone reactant, the ketone is gradually fed to the reaction over time to keep its concentration low.

In accordance with this invention there is provided a process for preparing a cyclopentenone, which process comprises forming a two-phase mixture of a water immiscible organic solvent and an aqueous base solution and feeding a 1,4-diketone to said mixture while heating said mixture so as to convert the 1,4-diketone to a cyclopentenone which collects in the organic solvent phase.

The 1,4-diketone reactants for use in the process of the invention can be prepared as known in the art, for example, see Rosini G. et al. *Tetrahedron*, 39 (24) 4127–32 (1983).

Preferred 1,4-diketones have the formula $CH_3COCH_2CH_2COCH_2R$ where R is hydrogen or a hydrocarbyl group which contains 1 to 15 carbon atoms. Non-limiting examples of hydrocarbyl groups include alkyl, substituted alkyl, aryl, substituted aryl, alkenyl, substituted alkenyl, and the like such as methyl, ethyl, propyl, isopropyl, butyl, isobutyl, tert-butyl, pentyl, hexyl, cyclohexyl, pentenyl, benzyl, phenyl, and naphthyl.

The reaction mixture is a two-phase system which includes an aqueous phase and an organic solvent phase.

The aqueous phase comprises an aqueous solution of a base such as an alkali or alkaline earth metal hydroxide solution, for example, sodium or potassium hydroxide. Preferably, sodium hydroxide is used in amounts to provide a 0.5 to 5 molar aqueous NaOH solution.

The organic solvent phase comprises a substantially water immiscible organic solvent, preferably hydrocarbyl or hydrocarbyl halide solvents and mixtures thereof having a boiling point of from about 25° to 250° C. Non-limiting examples of solvents include aromatic solvents such as toluene, xylenes, benzene, mesitylene, and the like and aliphatic solvents such as cyclohexane, hexanes, heptanes, octanes, methylene chloride, methylene bromide, ethylene dichloride, ethylene dibromide, and the like. The lower boiling solvents, can be employed in a closed system.

The proportions of water and organic solvents in the two phase system preferably range from about 0.5 to 10 parts by volume water per part by volume of organic solvent. The proportion of ketone reactant to base preferably ranges from about 0.5 to 5 moles of ketone per mole of base.

The reaction is carried out with mixing to promote contact between the phases at temperatures of from about 50 to 100° C. and preferably from about 70° to 90° C. The organic solvent and aqueous base solutions are charged to the reactor and heated to reaction temperature. The 1,4-diketone reactant is then slowly fed to the reactor either continuously or incrementally over a period of time of from about 0.5 to 5 hours or more, preferably from 1.5 to 3.5 hours, depending upon the size of the charge (feed rates of from about 30 to 300 pounds per hour or more). After the reactant feed is completed, the mixture is held at reaction temperature until substantially complete conversion of the ketone is obtained $\geq 95$ mole %. Yields of product of about 75 mole % based on ketone reactant, or higher with further optimization of conditions, with low tar formation can be obtained. Typical total reaction times range from about 0.5 to 20 hours.

During the reaction, the cyclopentenone product collects in the organic solvent phase such that product contact with the base is minimized. In this way, product decomposition due to such contact is reduced. Higher base concentrations aid in the "salting out" of the product into the organic phase. When the reaction is complete, the product can be recovered from the organic phase by conventional techniques such as by washing the organic layer with water or aqueous, saturated NaCl to reduce the pH to about 9 and then removing the organic solvent such as by vacuum stripping. The aqueous base layer can be extracted with an organic solvent to recover any product which remains in the aqueous layer. To dry the 3-MCP, solvent is stripped under vacuum and refluxed back to the reactor through a phase separator. Free water that collects in the bottom of the phase separator is drained out. This is continued until no more free water is collected overhead. The reflux is then shut off and a portion of the solvent is stripped out. The dry 3-MCP solution is then sampled and analyzed for moisture by low-current, coulometric Karl Fisher. This procedure typically reduces the water content to well below 100 ppm.

The invention is further illustrated by, but is not intended to be limited to, the following example.

EXAMPLE 1

To a 50-gallon stainless steel reactor equipped with an agitator were charged 147.2 pounds of toluene, 52 pounds of 25 wt. % aqueous sodium hydroxide and 26 pounds of water. The agitator was started and the reactor contents were heated to 190° F. (88° C.). Then 155 pounds of acetonylacetone (2,5-hexanedione) were slowly fed to the mixture over 3-½ hours, while maintaining the temperature near 190° F. The reactor was held at 190° F. for another 1-½ hours, then cooled to near room temperature. The mixture was then settled, and the aqueous caustic phase was removed. The organic phase was then washed with 100 pounds of 20 wt. % aqueous sodium chloride and another phase cut was done. 268.4 Pounds of 3-methylcyclo-pent-2-en-1-one (3-MCP) crude solution were obtained at 35.94 wt. percent 3-MCP, a yield of 73.9% based on the acetonylacetone charge.

Six batches run using the above semi-batch procedure had yields ranging from 70.7–75.3%. Eight runs made using a procedure in which all the acetonylacetone was charged to the reactor along with the solvent and aqueous base as described in U.S. Pat. No. 5,276,199 produced yields ranging from 61.1–66.8%. This demonstrates the yield advantage of the process of the invention. Reduced levels of about 30% less "tars" were obtained which would be expected to improve later processing steps. The runs made according to process of the invention also washed much easier. The salt-water wash typically reduced pH to about 8.5, whereas on the comparative runs where the acetonylacetone was precharged, the pH was often as high as 10–11, necessitating a second wash.

What is claimed is:

1. A process for preparing a cyclopentenone, which process comprises:

a) forming a two-phase mixture of a water-immiscible solvent and an aqueous base solution;

b) feeding a 1,4-diketone to said mixture continuously or incrementally over a period of time of at least about 0.5 hour while heating said mixture so as to convert the 1,4-diketone to a cyclopentenone which collects in the organic solvent phase, and c) after completing the feed, continuing to heat the mixture until substantially complete conversion of the ketone is obtained.

2. The process according to claim 1 wherein said 1,4-diketone has the formula $CH_3COCH_2CH_2COCH_2R$, where R is hydrogen or a hydrocarbyl group which contains from 1 to about 15 carbon atoms.

3. The process according to claim 2 wherein R is hydrogen and said cyclopentenone is 3-methylcyclopent-2-en-1-one.

4. The process according to claim 1 wherein said aqueous base solution is an aqueous sodium hydroxide solution.

5. The process according to claim 4 wherein said aqueous base solution is from about a 0.5 to 5 molar aqueous sodium hydroxide solution.

6. The process according to claim 5 wherein said organic solvent is a hydrocarbyl or hydrocarbyl halide solvent.

7. The process according to claim 6 wherein the proportions of water and organic solvent range from about 0.5 to 10 parts by volume water per part by volume of organic solvent.

8. The process according to claim 1 wherein said mixture is heated to a temperature of from about 50° to 100° C.

9. The process according to claim 1 wherein the molar proportion of 1,4-diketone to base ranges from about 0.5 to 5 moles of 1,4-diketone per mole of base.

10. A process for making 3-methylcyclopent-2-en-1-one, which process comprises forming a two-phase mixture of a water immiscible organic solvent and an aqueous alkali metal base solution and slowly feeding acetonylacetone to said mixture while heating said mixture at a temperature of from about 70° to 90° C. so as form 3-methylcyclo-pent-2-en-1-one which collects in the organic solvent phase.

11. The process according to claim 10 wherein said aqueous alkali metal base solution is 0.5 to 5 molar aqueous sodium hydroxide and said mixture contains from about 0.5 to 5 moles of acetonylacetone per mole of sodium hydroxide.

12. The process according to claim 11 wherein said organic solvent is selected from toluene and methylene bromide.

13. The process according to claim 10 wherein said acetonylacetone is fed to said mixture over a period of time of at least about 0.5 hour.

14. A process for preparing a cyclopentenone, which process comprises:

a) forming a two-phase mixture of (i) a water-immiscible organic solvent selected from the group consisting of water-immiscible hydrocarbon solvents and water-immiscible halohydrocarbon solvents, and (ii) an aqueous base solution selected from the group consisting of aqueous alkali metal hydroxide solutions and aqueous alkaline earth metal hydroxide solutions;

b) feeding to said two-phase mixture a 1,4-diketone of the formula $CH_3COCH_2CH_2COCH_2R$, where R is a hydrogen atom or a hydrocarbyl group which contains from 1 to about 15 carbon atoms, the feeding being conducted continuously or incrementally over a period of time of about 0.5 to about 5 hours while mixing the resultant mixture, and the total amount of 1,4-diketone fed being equivalent to a molar ratio of from about 0.5 to about 5 moles of 1,4-diketone per mole of base;

c) heating the mixture being formed in b) at a temperature in the range of about 50° to 100° C. so as to convert the 1,4-diketone to a cyclopentenone which collects in the organic solvent phase; and d) after completing the feed in c), continuing to heat the mixture until substantially complete conversion of the ketone is achieved.

15. A process in accordance with claim 14 wherein said 1,4-diketone is acetonylacetone, wherein said aqueous base solution is an aqueous sodium hydroxide or aqueous potassium hydroxide solution, and wherein said temperature is in the range of about 70° to about 90° C.

\* \* \* \* \*